(12) United States Patent
Atterbury et al.

(10) Patent No.: US 11,957,878 B2
(45) Date of Patent: Apr. 16, 2024

(54) PROCESS AND AUTOINJECTOR DEVICE FOR INJECTIONS WITH INCREASED PATIENT COMFORT

(71) Applicant: Battelle Memorial Institute, Columbus, OH (US)

(72) Inventors: William G. Atterbury, Columbus, OH (US); Douglas E. Boyd, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 357 days.

(21) Appl. No.: 17/342,530

(22) Filed: Jun. 8, 2021

(65) Prior Publication Data
US 2021/0369965 A1 Dec. 2, 2021

Related U.S. Application Data

(62) Division of application No. 15/742,507, filed as application No. PCT/US2016/041189 on Jul. 6, 2016, now Pat. No. 11,052,195.
(Continued)

(51) Int. Cl.
*A61M 5/20* (2006.01)
*A61M 5/315* (2006.01)
*A61M 5/32* (2006.01)

(52) U.S. Cl.
CPC .......... *A61M 5/2033* (2013.01); *A61M 5/326* (2013.01); *A61M 5/3287* (2013.01);
(Continued)

(58) Field of Classification Search
CPC .. A61M 5/2033; A61M 5/326; A61M 5/3287; A61M 5/3155; A61M 5/31583;
(Continued)

(56) References Cited

U.S. PATENT DOCUMENTS 7,195,616 B2 3/2007 Diller et al.
8,052,655 B2 11/2011 Møller et al.
(Continued)

FOREIGN PATENT DOCUMENTS

CH 711240 A2 12/2016
WO 2009081133 A1 7/2009
(Continued)

OTHER PUBLICATIONS

Machine Translation of the Description of CH 711240 A2.
(Continued)

*Primary Examiner* — Ariana Zimbouski
*Assistant Examiner* — Rachel T. Smith
(74) *Attorney, Agent, or Firm* — Susanne A. Wilson; Frank Rosenberg

(57) ABSTRACT

The invention provides methods and apparatus for injecting a medicine, especially a highly viscous medicine. Conventional methods and apparatus for injecting viscous medicines suffers suffer from a variety of problems such as excessive force during the initial needle insertion and initial injection. In an inventive method, during the initial phase of the injection, energy is stored in a torsion spring that is subsequently released during a later stage of the injection. The present invention also provides for an improved autoinjector; especially via the use of a combination compression and torsion spring that powers the injection through controlling force applied to a plunger via a screw flange or nut having pins that ride in a prescribed path down the length of the autoinjector.

19 Claims, 16 Drawing Sheets

Related U.S. Application Data

(60) Provisional application No. 62/189,134, filed on Jul. 6, 2015.

(52) U.S. Cl.
CPC .............. *A61M 2005/206* (2013.01); *A61M 2005/2073* (2013.01); *A61M 5/3155* (2013.01); *A61M 5/31583* (2013.01)

(58) Field of Classification Search
CPC .... A61M 2005/206; A61M 2005/2073; A61M 2005/2026
See application file for complete search history.

(56) References Cited

U.S. PATENT DOCUMENTS

| | | |
|---|---|---|
| 8,702,660 B2 | 4/2014 | Karlsson |
| 8,734,394 B2 | 5/2014 | Adams et al. |
| 8,808,250 B2 | 8/2014 | Ekman et al. |
| 9,011,387 B2 | 4/2015 | Ekman et al. |
| 9,814,836 B2 | 11/2017 | Cowe |
| 2014/0039409 A1 | 2/2014 | Radmer et al. |

FOREIGN PATENT DOCUMENTS

| | | | | |
|---|---|---|---|---|
| WO | WO-2009081133 A1 | * | 7/2009 | .......... A61M 5/2033 |
| WO | 2011060786 A1 | | 5/2011 | |
| WO | WO-2011101383 A1 | * | 8/2011 | .............. A61M 5/20 |
| WO | WO-2011109205 A2 | * | 9/2011 | .............. A61M 5/20 |

OTHER PUBLICATIONS

International Preliminary Report on Patentability from International Application No. PCT/US2016/041189 dated Jan. 9, 2018.
Written Opinion of the International Search Authority from International Application No. PCT/US2016/041189 dated Oct. 10, 2016.
International Search Report from International Application No. PCT/US2016/041189 dated Oct. 10, 2016.
Office Action in European Patent Application No. EP16738997.2A dated May 30, 2022.

* cited by examiner

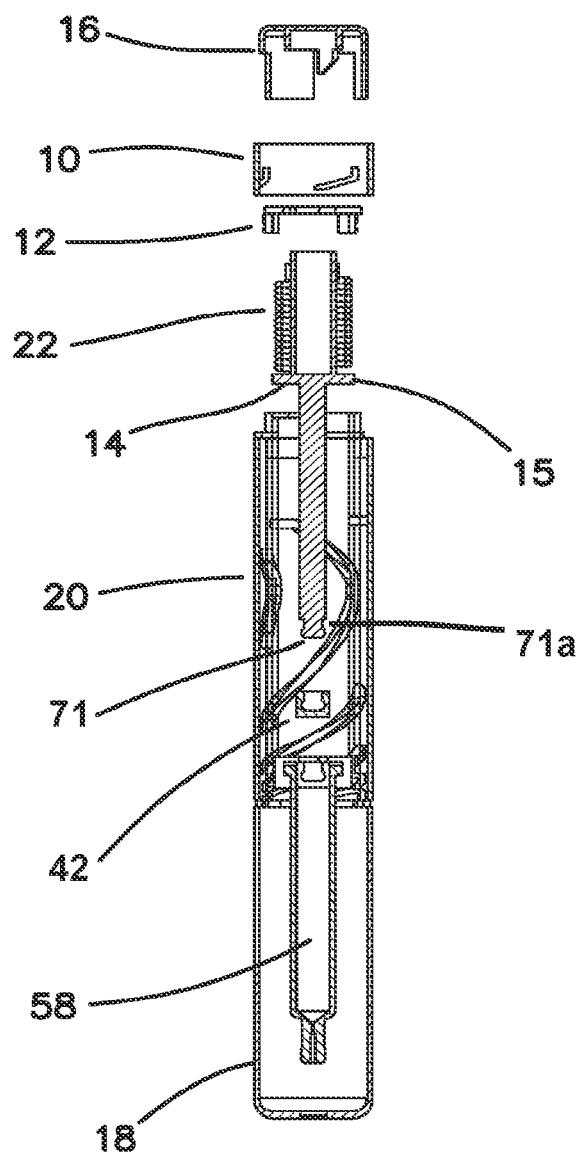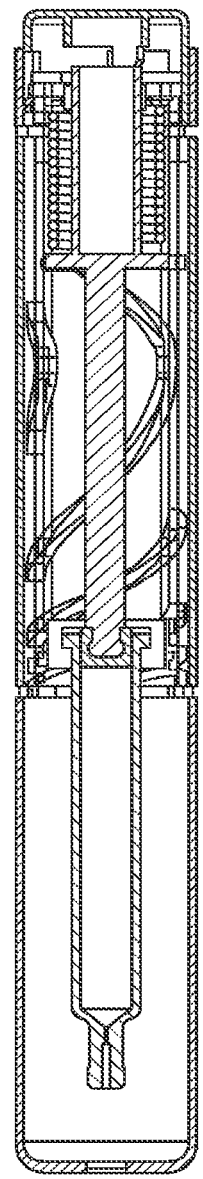
FIG. 1
FIG. 2B

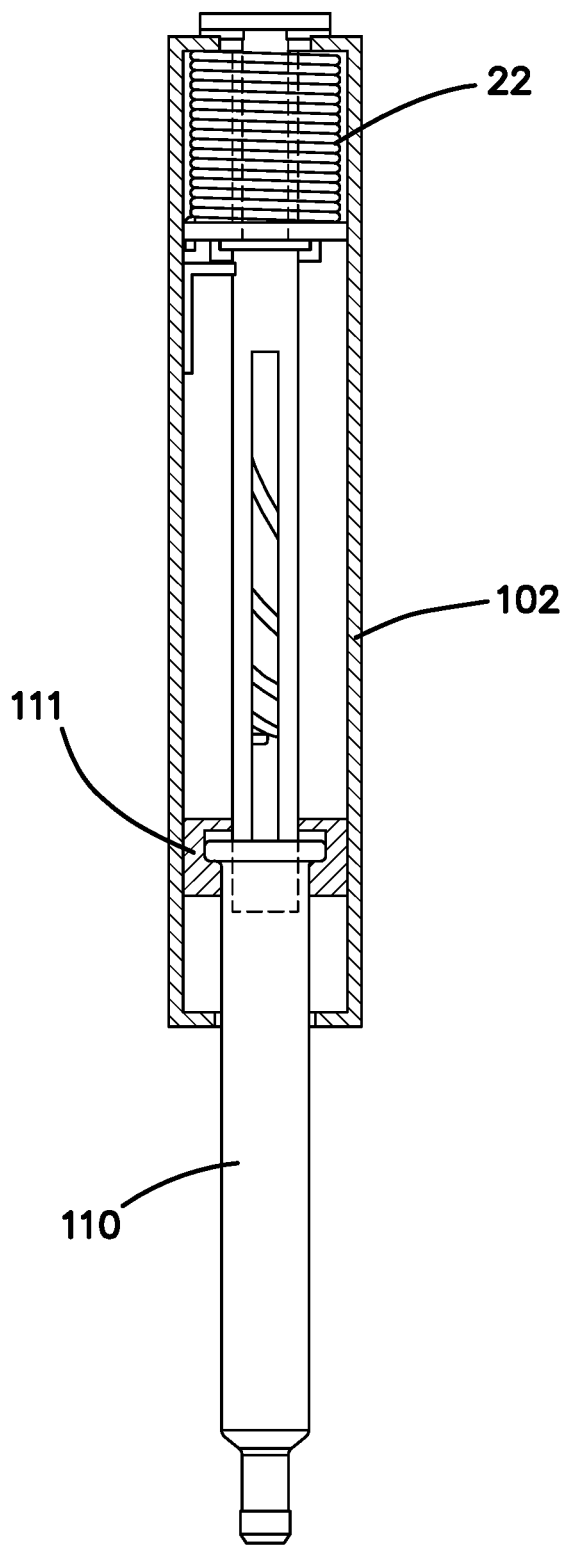
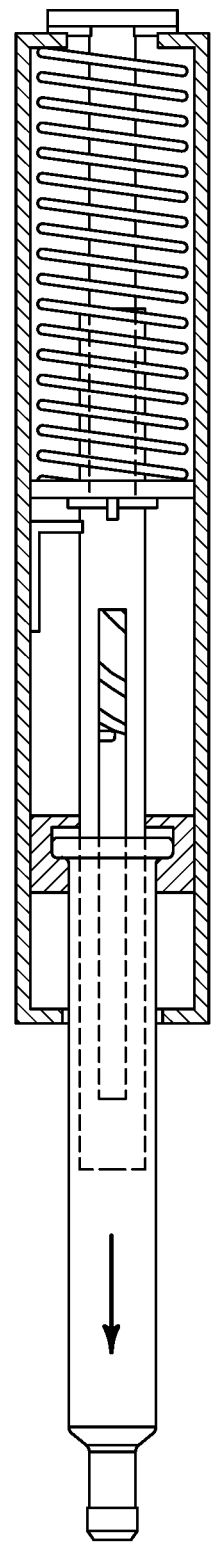
FIG. 10
FIG. 11

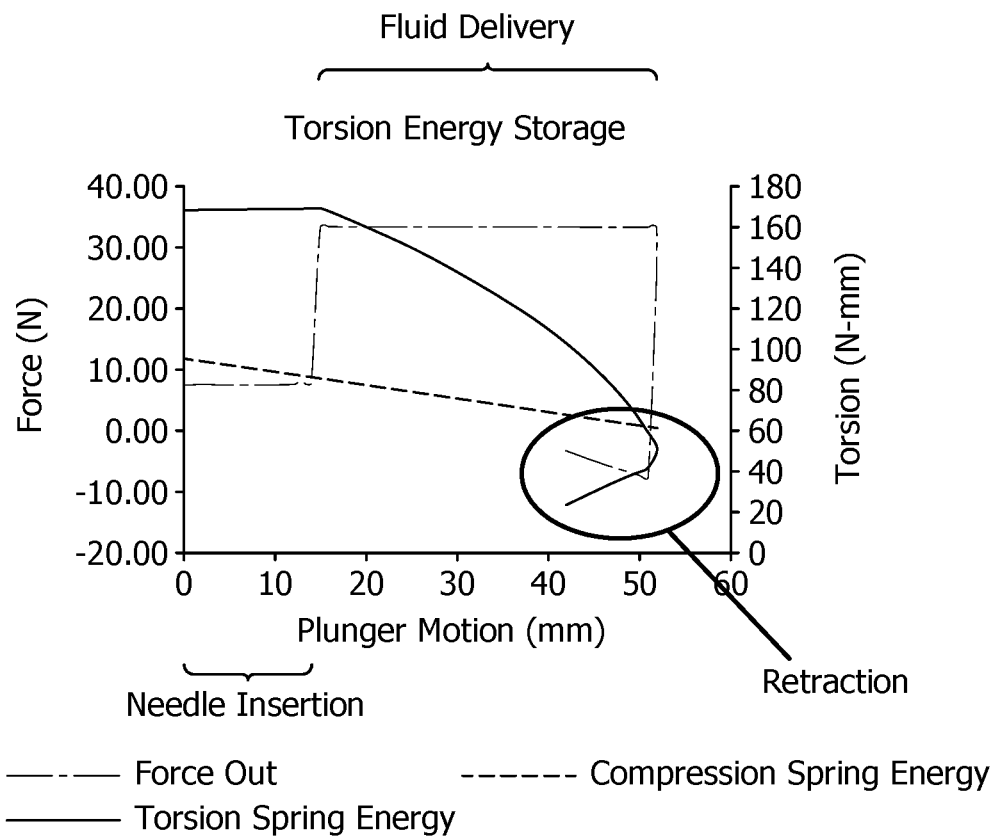
FIG. 18
FIG. 19
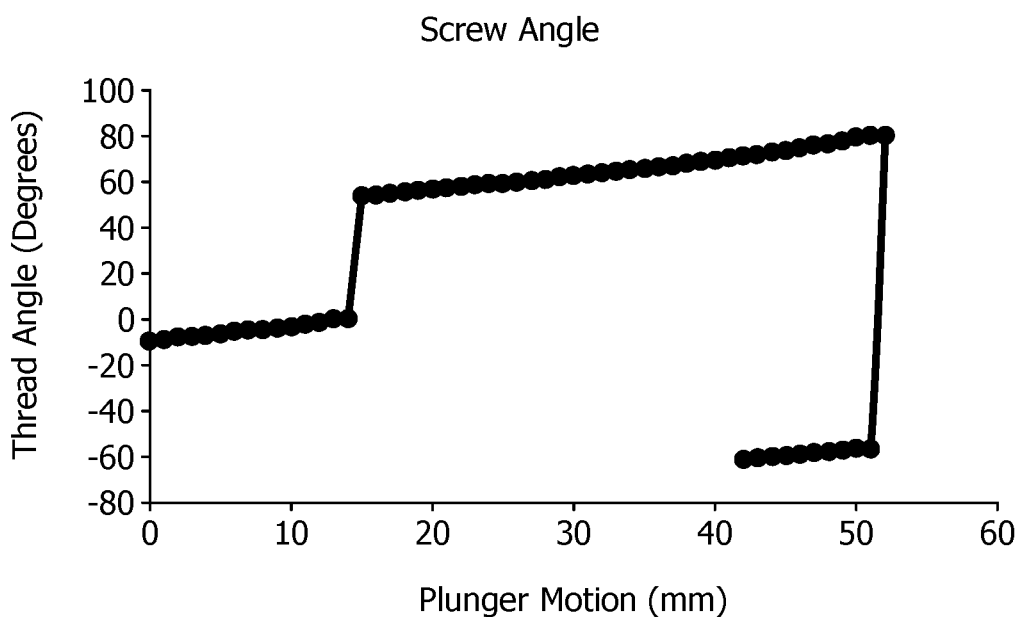

PROCESS AND AUTOINJECTOR DEVICE FOR INJECTIONS WITH INCREASED PATIENT COMFORT

RELATED APPLICATION

This application is a divisional of U.S. patent application Ser. No. 15/742,507 filed 6 January 2018 and claims the priority benefit of PCT/US16/41189 which is incorporated herein by reference and also claims the priority benefit of U.S. Provisional Patent Application Ser. No. 62/189,134, filed 6 Jul. 2015.

INTRODUCTION

Injections continue to be a very important mode of delivering medications. Injections are especially important, yet difficult, for high viscosity solutions such as protein compositions. Protein therapeutics is an emerging class of drug therapy that promises to provide treatment for a broad range of diseases, such as autoimmune disorders, cardiovascular diseases, and cancer. Delivery of protein therapeutics is often challenging because of the high viscosity and the high forces needed to push such formulations through a parenteral device. Formulations with absolute viscosities above 40-60 centipoise (cP) are very difficult to deliver by conventional spring driven autoinjectors for multiple reasons. For example, many current autoinjectors are relatively large or complex. For spring-loaded autoinjectors, a large amount of energy must be stored in the spring to reliably deliver high-viscosity fluids. An autoinjector typically operates by using the spring to push a needle-containing internal component towards the proximal end of the housing of the syringe, thereby extending the needle from the device and inserting it to the proper depth into the patient. Most autoinjectors use the same spring to insert the needle as is used to deliver the medicament. The injection depth depends on stopping a rapidly moving needle in a precise location. Autoinjectors usually contain glass or plastic parts, and excessive and sudden forces could cause the injector and/or syringe to break, due to the high applied force needed to inject a high-viscosity fluid. Some drugs can be affected by the violent mixing with air. Also, the sound and vibration associated with the impact can cause patient anxiety, reducing future compliance.

Over the years, extensive efforts have been expended on developing improved injection methods and spring-powered autoinjectors. Most autoinjectors have used a compression spring to power the expulsion of medication from a syringe. Another method that has been proposed for powering an autoinjector is the use of a torsion spring. For example, Karlsson in U.S. Pat. No. 8,702,660 describes an autoinjector in which a torsion spring inside the autoinjector can be tensioned by the user by means of a tensioning wheel to deliver a desired dose. The torsion spring applies force to a drive nut that is engaged with threads of a plunger rod. The plunger rod then expels medication through the needle.

Ekman et al. in U.S. Published Patent Application No. 20130123697 describes an autoinjector with a torsion spring that is used for inserting the needle, emptying the syringe and then retracting the needle and syringe. The autoinjector is activated by pressing a trigger button that releases the torsion spring to exert a force on a stopper and syringe. Eckman et al. report that the lead screw thread has a variable pitch arranged to advance a second gear member faster and with less force when inserting the needle (steep pitch) and more slowly with increased force while expelling the medicament in the syringe.

Cowe in WO/2012/038721 describes a reusable autoinjector that can be rewound and reused. Cowe also provides a rotary energy source such as a torsion spring. The disclosure is primarily directed to a constant pitch screw thread, although Cowe mentions the possibility of a nonuniform pitch to provide a desired variable force profile.

Adams et al. in U.S. Pat. No. 8,734,394 describes an autoinjector that uses a helically coiled wire to perform delay and needle retraction functions. The spring, referred to as a dual functioning biasing member, performs these two tasks independently and sequentially, first in rotation turning a component immersed in a damping fluid to achieve a prescribed delay time, and second in extension to retract the syringe and needle subassembly.

Despite these and other efforts, there remains a need to develop injection methods and autoinjectors with improved characteristics such as relatively simpler or more compact designs, smoother injection, and/or less noise.

SUMMARY OF THE INVENTION

The primary problem with spring-loaded autoinjectors is that either the initial force is too great or the force at the latter stages of the injection is too weak. We have developed a simple and elegant solution to this problem by utilizing a spring in a manner that tailors the release of energy as the spring is extended. The spring first advances the syringe and needle forward in a controlled manner with the objective of minimizing needle insertion force. The spring subsequently delivers the medicament using a higher force with a profile tailored to suit optimum delivery. One embodiment utilizes a nearly constant delivery force profile that stands in contrast to the decreasing force profile of conventional coil springs.

Advantages of various embodiments of the invention include one or a combination of: reduced initial force during needle insertion and correspondingly less noise and less shock to the patient; reduced sudden impact to the syringe and reduced chance of breakage; reduced sudden acceleration of the viscous medicine within the syringe and needle; the ability to tailor flow for greater patient comfort and/or desired injection profile; reduced injection time; and/or less tissue disruption or trauma at injection site.

In a first aspect, the invention provides a method of injecting a medicament from a syringe, comprising: providing a driving force that moves a plunger down a syringe from a distal position toward a proximal position; wherein a torsion spring is attached at a distal end to a first surface and at a proximal end to a second surface; wherein the second surface moves with the plunger; wherein an early stage movement of the plunger toward the proximal position twists the torsion spring to store energy in the spring; and, subsequently, at a later stage, as the driving force continues to move the plunger toward the proximal position, and the second surface moves with the plunger, the torsion spring rotates through a prescribed path to modify the driving force moving the plunger toward the proximal position. The path can be prescribed by the design of a plunger movement assembly (PMA) described below in an aspect describing injector apparatus.

In some embodiments, the torsion spring is a combination torsion and compression spring. The use of a combination torsion and compression spring in the present invention provides numerous advantages including reduced friction losses.

The invention may have one or any combination of the following features: wherein the combination torsion and compression spring is the only source of providing the driving force; wherein, during the later stage, the torsion spring is untwisted to enhance the driving force; wherein, once activated, the injection occurs without any power source other than the spring; wherein the early stage movement corresponds to an initial period of syringe motion in which the driving force is relatively low in order to insert the needle into the patient's skin (for example between about 5% to 50% of the maximum driving force and/or the average force (averaged either over the time of injection or the distance of injection) or between about 10% and about 40%, or between about 10% and 30%, or between about 15% and 30%) and in preferred embodiments this initial period is from activation of the autoinjector to 5 ms or 50 ms or 100 ms (milliseconds) after activation, or from 0 to 5 mm, or 0 to 10 mm of plunger motion; or wherein during the initial phase the driving force is from 1 to 20 Newtons (N), or from 2 to 10 N, or from 3 to 7 N; or any combination of these; where potential torsion energy in the spring is increased over the first 50 or 100 ms after activation, or from 0 to 5 mm, or 0 to 10 mm, or from 0 to about mm, or from about 0 to 25 mm; wherein potential torsion energy in the spring reaches a maximum at about 10 mm and/or about 7 ms (or between 5 ms and 50 ms) after activation, or between about 5 and 50 mm, or between about 5 mm and 30 mm, or between about 5 mm to 20 mm after activation; or between about 5% to about 40% of the full distance traveled during the injection; wherein the potential torsion energy in the spring increases at least 5 N·mm or at least N·mm, or between 10 and 500 N·mm, or between 15 and 300 N·mm, or between 20 and 200 N·mm; wherein the spring is preloaded with both torsion energy and compression energy; wherein the initial potential compression energy is greater than the initial potential torsion energy; wherein the potential compression energy in the torsion spring decreases approximately linearly as a function of plunger motion; or wherein, during the second half of the injection (either by time or by plunger motion) the percentage of potential torsion energy in the spring decreases at a rate faster than the percentage of potential linear energy; or wherein, after the initial phase, the driving force increases rapidly, for example, increasing at least 10 N or wherein driving force at least doubles or at least triples, over a distance of 5 mm, or 2 mm, or less, or between 0.1 to 3 mm of plunger motion, or a time of 1 s or less or between 20 ms and 1 s, or between 5 ms and 500 ms; or any combination of these; wherein the later stage movement defines an injection phase, and wherein the driving force is reduced by less than 50%, more preferably less than 40%, or less than 20% or between 10 and 40%, or between 5 and 30% during the injection phase; or wherein the driving force is remains between 10 and 200 N, or between 10 and 40 N, or between 20 and 80 N, or between 20 and 40 N during the injection phase; wherein, from an activation step through the end of the injection phase, the potential compression energy in the spring is reduced by at least 40%, or at least 50% or from 30% to 90%; and/or wherein the first surface is an internal surface of the distal end of an autoinjector housing.

The inventive methods may further comprise a retraction stage, subsequent to the later stage, in which the spring pulls the plunger in the distal direction. In some preferred embodiments, the second surface is on a nut, the spring is attached to the nut and the prescribed path is controlled by a screw having helical threads; the nut has a pin or pins that ride in the threads of the screw; wherein, during the retraction stage, the pin or pins ride in the threads in a distal direction and wherein the spring provides a torque having a force component in the direction in which the pin or pins ride. In some embodiments, the spring is attached to a nut and the prescribed path is controlled by a screw having helical threads; wherein the nut has a pin or pins that ride in the threads of the screw; wherein the helical threads have a thread angle $\alpha$ that varies along the length of the screw (see FIG. 23). In some preferred embodiments, friction occurs between the pin or pins and the screw, wherein during at least a portion of the later phase, the spring supplies a torque that has a force component perpendicular to length in the direction of the threads of the screw. This serves to reduce friction as compared to a compression-only spring.

In a related aspect, the invention provides a method of injecting a medicament from a syringe, comprising: providing a driving force that inserts a needle at the proximal end of the device, then subsequently moves a plunger down a syringe from a distal position toward a proximal position; wherein a spring having both a torsion mode and a compression mode is attached at one end to a first surface and at one end to a second surface; wherein the second surface moves with the plunger and an early stage movement of the plunger toward the proximal position twists the torsion spring to store energy in the spring; and subsequently as the driving force due to the compression mode continues to move the plunger toward the proximal position, and the second surface moves with the plunger, the torsion mode of the spring rotates through a prescribed path to modify the driving force moving the plunger toward the proximal position. In various preferred embodiments of this aspect, the insertion of the needle is accomplished by transferring energy from the compression mode of the spring to the torsion mode spring in order to optimize force needed for needle insertion; wherein the energy is released from the compression spring by changing the length of the spring and the energy is added to the torsion mode of the spring by increasing the number of winds of the spring; where the coil spring wire has a round cross section; where the coil spring wire has a square cross section in order to increase the amount of stored energy possible in a given package size; wherein the step in which the torsion mode of the spring rotates through a prescribed path to modify the driving force comprises untwisting the spring to release energy from the spring to enhance the driving force moving the plunger toward the proximal position; and/or where the coil spring wire has a rectangular cross section in order to optimize the relationship of the compression and torsion characteristics of the spring.

In another aspect, the invention provides an injector apparatus, comprising:
an elongate outer casing having a distal end and a proximal end; a plunger movement assembly (PMA), comprising:
  (a) a screw axially disposed within the outer casing;
  the screw having helical threads;
  a nut wherein the nut has a pin or pins that ride in the threads of the screw;
  wherein the screw has external threads and the nut is disposed around the screw; and
  a combination compression and torsion spring that is connected at the distal end to the casing and connected at the proximal end to the nut;
  a plunger rod connected to the proximal end of the nut; or
  (b) a nut comprising an axial central cylindrical orifice having helical grooves;
  a screw flange disposed within the central cylindrical orifice having a pin or pins that ride in the helical grooves;

a plunger rod connected to the screw flange; and
a combination compression and torsion spring that is connected at the distal end to the casing and connected at the proximal end to the screw flange;
a syringe adapted for containing a medicament attached to the outer casing and/or a proximal end of the PMA; and wherein the proximal end of the plunger rod is slide-ably disposed within the syringe.

In various preferred aspects, the injector apparatus comprises one or any combination of the following features: the injector apparatus having the PMA of type (a) wherein the screw having helical threads comprises threads in a first portion that turn in a first direction, and that turn in a second direction in a second portion; and wherein the nut has a pin or pins that ride in the threads of the screw such that the nut turns in the first direction in the first portion and in the opposite direction in the second portion (for example clockwise and counterclockwise); a hollow needle disposed at the proximal end of the syringe; an injector having the PMA of type (b) wherein the nut having helical grooves comprises grooves in a first portion that turn in a first direction, and that turn in a second direction in a second portion; and wherein the screw flange has a pin or pins that ride in the grooves of the nut such that the screw flange turns in the first direction in the first portion and in the opposite direction in the second portion (for example clockwise and counterclockwise); wherein the first portion is nearer the distal end and the second portion is nearer the proximal end; wherein the proximal tip of the plunger rod is rotatably disposed within a plunger cap; wherein the proximal end of the plunger rod is rotatably disposed within a plunger cap by a jewel bearing; wherein the plunger rod has a proximal tip 71 that abuts a surface of the plunger cap and a restricted neck portion 71a; and wherein the plunger cap has a distal end having flanges that project inwardly toward the central axis; wherein a syringe carrier retains the syringe within a housing; wherein in the first portion, the screw angle is in the range of −70 to −20 degrees, in some embodiments from −60 to −30 degrees; then for the second portion, the screw angle is positive, in some embodiments 10 degrees or more, in some embodiments in the range between 10 and 80 degrees; wherein in the first portion, the screw's lead is negative and in some embodiments is between 10 and 120 mm, in some embodiments between 20 and 80 mm, or between 30 and 70 mm; wherein the lead decreases during the first portion, in some preferred embodiments, this decrease is approximately monotonic, preferably with a decrease of about 5 mm to about 40 mm; wherein in the second portion the screw lead is positive for at least a portion of the injection, preferably for the entire injection, and is preferably between 2 and 500 mm, in some embodiments between 10 and 300 mm, or between 15 and 200 mm; in some embodiments, the lead decreases during the second portion, in some preferred embodiments, this decrease is approximately monotonic, preferably with an decrease of at least about 20 mm or at least about 50 mm, or in the range of about 20 mm to about 300 mm, or 10 mm to 150 mm over the length of the second portion; and/or wherein the screw lead decreases during the second portion from about 170±40 mm to about 20±40 mm over the length of the second portion. In a preferred embodiment, the helical threads have a first direction at the distal end and the spring has a wind direction which is opposite that of the first direction. This configuration can be advantageous for securing the ends of the spring.

In a preferred embodiment, the helical threads have a first direction at the distal end; and, at the proximal end, have threads having a second direction that causes the needle to move in the distal direction thereby causing the needle to retract and lock into a stored location.

In another aspect, the invention provides a method of injecting a medicament from a syringe, comprising: providing a driving force that moves a plunger along an axis from a distal position toward a proximal position down a syringe; wherein a combination compression and torsion spring is attached at a distal end to a first surface and at a proximal end to a second surface; wherein the second surface moves with the plunger; wherein the second surface is on a nut such that the spring is attached to the nut; wherein the nut has a pin or pins that ride in the threads of a screw having helical threads; wherein the spring provides a torque having a force component that is perpendicular to the axis and is in a direction in which the pin or pins ride toward the proximal position; wherein the combination of the energy stored in compression and torsion is released in a prescribed manner based on the distance between the distal and proximal positions. The first surface is typically on the housing of an autoinjector.

In many cases, the invention does not require features such as: a secondary compression spring for tasks such as needle insertion; a viscous damping fluid to reduce insertion speed; operation in conjunction with a pressurized gas; however, in some aspects, the invention may utilize one or more of these features.

Glossary

A torsion spring is an elastic object that stores mechanical energy when it is twisted. A preferred form of a torsion spring is a helical wire. A compression spring stores energy when compressed and then releases that energy when the spring is released, and is preferably in the form of a helical wire. An extension spring is an elastic material (typically a helical spring) that stores energy when extended and releases that energy when the spring is released.

A compression spring is defined as a spring that, in its first released state, can be compressed by at least 10% (preferably at least 50%) and again released to recover at least 95% (preferably at least 99%) of its length in the first released state. A torsion spring, according to the present invention, in its relaxed state can be twisted at least about 90° (quarter twist), more preferably at least a half twist, or in some embodiments at least a full twist, or between a quarter and a full twist, and then return to its initial position. A combination compression and torsion spring has the properties of both a compression spring and a torsion spring.

A medicament is also called a medicine.

The "driving force" is the axial force along the vector from the distal end to the proximal end that expels the medicine from the syringe (typically a conventional cylindrical syringe); and, typically, also pushes the needle through the skin of the patient.

A "jewel bearing" is a bearing in which an end of a plunger rod rotates freely without roller bearings.

The proximal end is the end of the device near the point where the needle enters the patient while the distal end is the opposite end that is furthest from the patient.

The first surface can be an inner surface of an enclosure which is typically an elongated container; alternatively it can be a stopper or any solid component (typically fixed in place) disposed within a container. The distal end of the torsion spring can be attached to the first surface by lodging the end within a notch or attachment mechanism that adheres the torsion spring to the first surface. The second surface is typically the distal end of a nut or plunger rod.

Various aspects of the invention are described using the term "comprising;" however, in narrower embodiments, the invention may alternatively be described using the terms "consisting essentially of" or, more narrowly, "consisting of."

BRIEF DESCRIPTION OF THE DRAWINGS

FIG. 1 illustrates an exploded side view of an autoinjector.

FIG. 2B illustrates a non-exploded side view of the autoinjector of FIG. 1.

FIG. 10 is a schematic cross-sectional view of an autoinjector prior to activation.

FIG. 11 is a schematic cross-sectional view of an autoinjector prior after activation.

FIG. 18 shows force and energy as a function of plunger motion during insertion, delivery and retraction.

FIG. 19 shows the relationship between thread (screw) angle and plunger motion.

DETAILED DESCRIPTION OF THE INVENTION

Figure 2A:
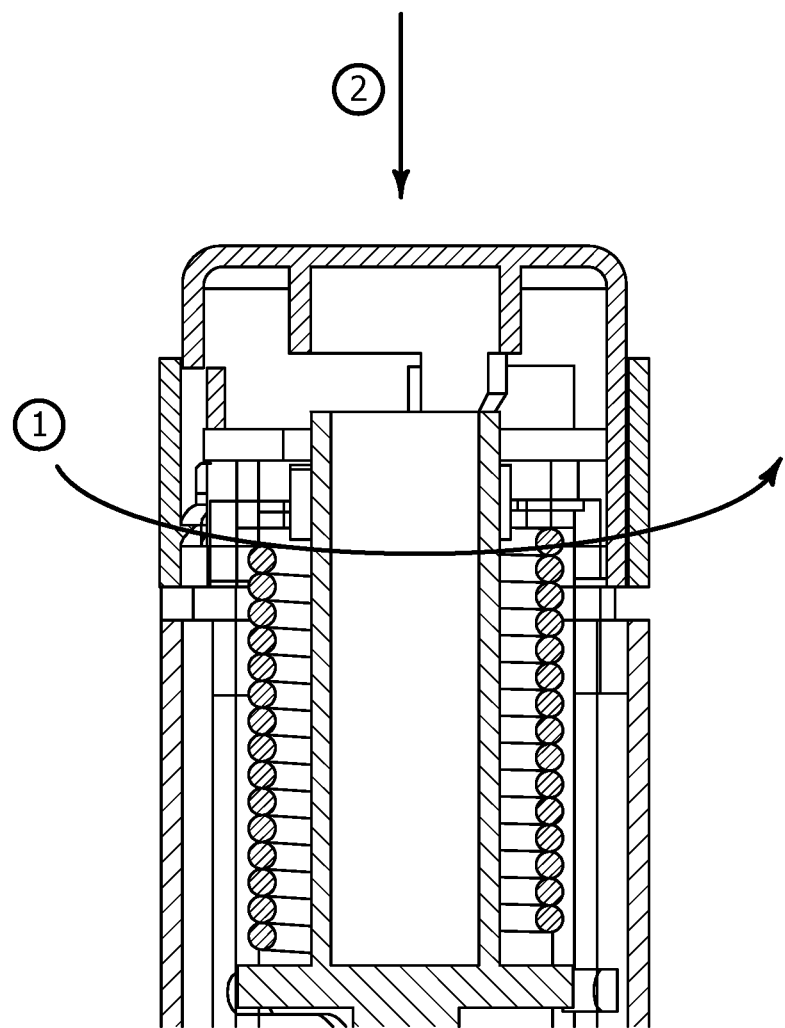
FIG. 2A illustrates device activation.
Figure 3:
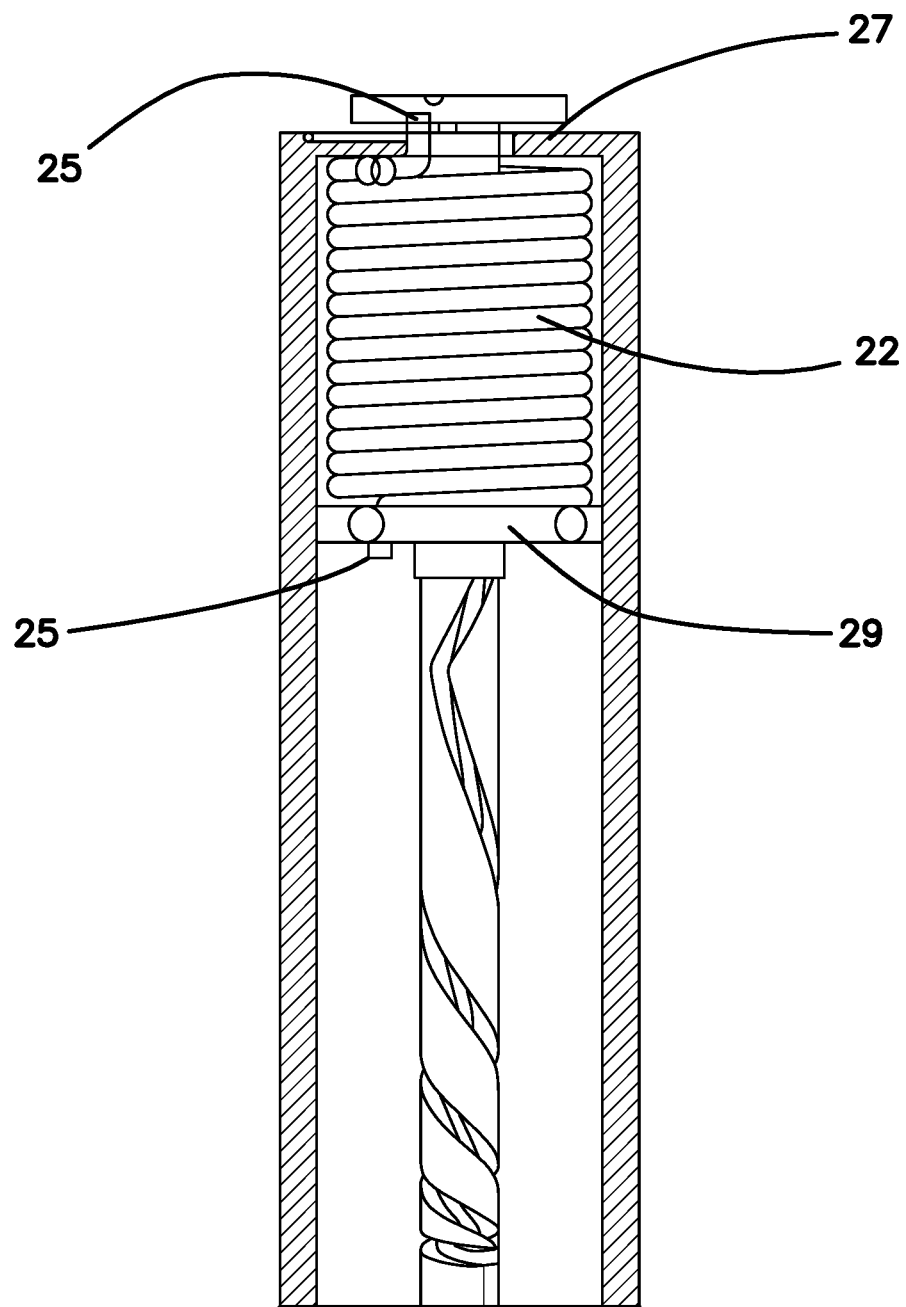
FIG. 3 is a schematic cross-sectional view of an autoinjector having a central, fixed screw.

FIGS. 1, 2A, 2B, 4A, 4B, 5, and 12 illustrate one embodiment of the invention. To operate the device, the user will typically remove it from packaging and allow it to equilibrate to room temperature if stored refrigerated. A sterile needle shield cover would be removed (not shown) to expose the needle. To use the device the user would first prepare the injection site (e.g., abdomen, thigh, arm) and locate the proximal end of the device against the injection site. To operate the device, the user turns the unlock collar. Turning (step 1 in FIG. 2A) the unlock collar 10 lifts the lock plate 12 using ramps 10a so the keyway 12a on the lock plate exits the key on the plunger screw 14a that includes screw flange 15. Turning the unlock collar also rotates the button 16 which moves the bottom of the button 16b away from the support ledge 20a and allows it to move freely in the axial direction. In this state, the device is unlocked, but will not actuate. To actuate the device, the user depresses the button 16 (step 2 in FIG. 2A). The ramps 16a on the button cause the plunger screw to rotate. The plunger screw 14 then travels both axially and rotationally down the nut due to both the force and torque applied by the drive spring 22. The initial portion of the movement inserts the needle into the patient's skin to the proper depth. After this depth is achieved, the remainder of the movement expels drug into the patient. Optionally, a needle retraction feature (discussed below) and safety lockout mechanism (not shown) could be added so that the device could be safely disposed of after use.

The device additionally comprises casing 18, which, in the illustrated embodiment, includes sleeve 20 and button 16 and lock plate 12. The invention is sometimes described as having a spring 22 connected to the sleeve 20; this means that the spring is either directly attached to the sleeve or attached to a stationary structure (such as an internal flange) that is, in turn, connected to the sleeve. The casing surrounds the sleeve which can be split into multiple pieces for improved manufacturability. Tabs 25 on the spring can be passed through holes in a suitable structure such as flange 27 and movable nut 29.

Figure 4A:
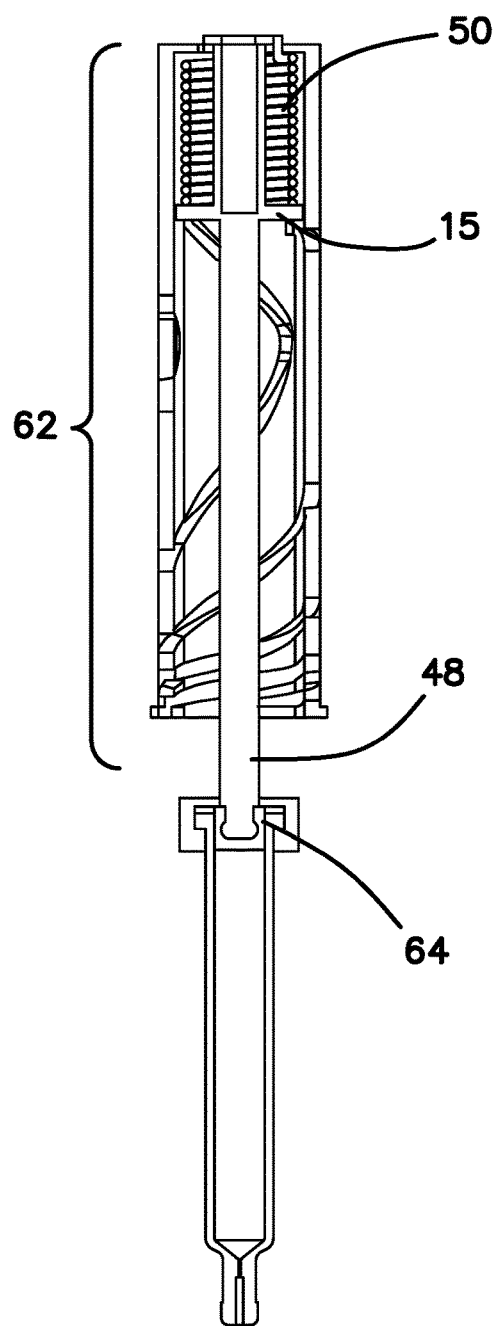
FIG. 4A illustrates a cross-sectional view of an autoinjector.
Figure 4B:
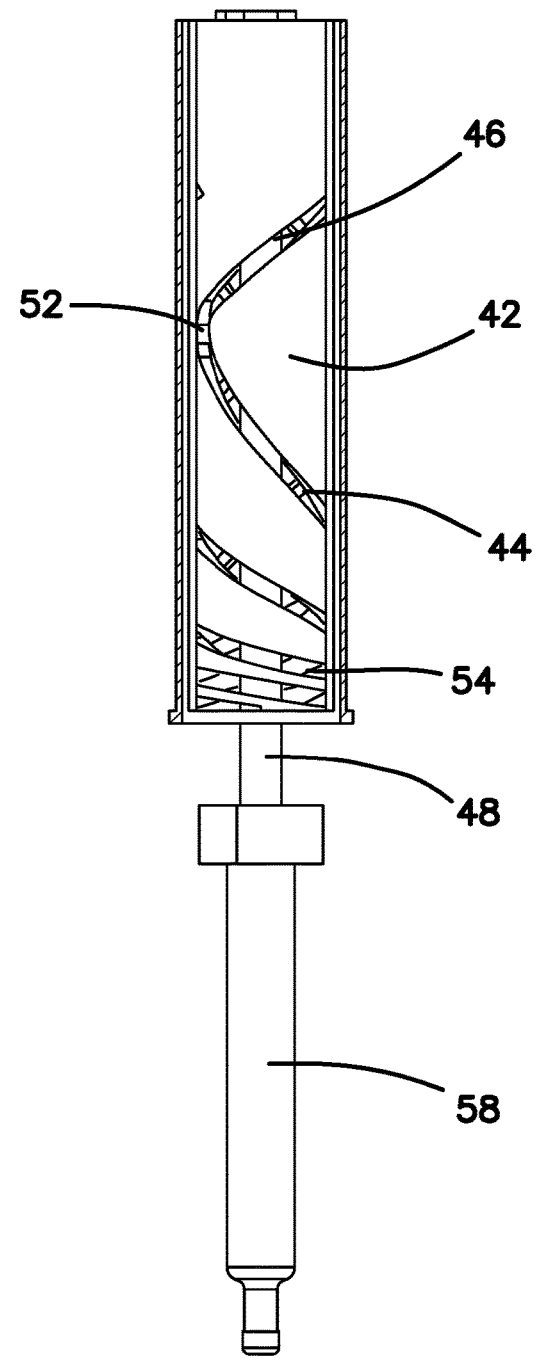
FIG. 4B illustrates an external view of an autoinjector.

FIGS. 4A and 4B show an outer view (right side, 4B) and cross-sectional view (left side 4A) of a portion of an injector including a nut 42 having grooves 44 that include an upper (first) portion having a relatively steep groove 46 in a direction that cooperates with screw flange 15 to slow the plunger 48 and store energy in torsion spring 50. At location 52, a knee in the groove reverses the twist direction of the torsion spring. In the lower (second) portion 54, the torsion spring untwists and releases energy into the spring to maintain a constant or nearly constant force that pushes the plunger into the syringe and thus maintains a constant flow of medicine out of the syringe throughout the injection. The release of energy is further aided by controlling the angles of the thread in the lower portion. The screw flange 15, plunger rod 48, torsion (or typically combination torsion and compression) spring 50, and nut 42 form a plunger movement assembly 62. Because the plunger screw 14 is rotated, it is desirable to have a bearing 64 to facilitate rotation of the plunger rod within the syringe 58. Another possibility is to place a bearing between the plunger rod and the screw flange.

Figure 5:
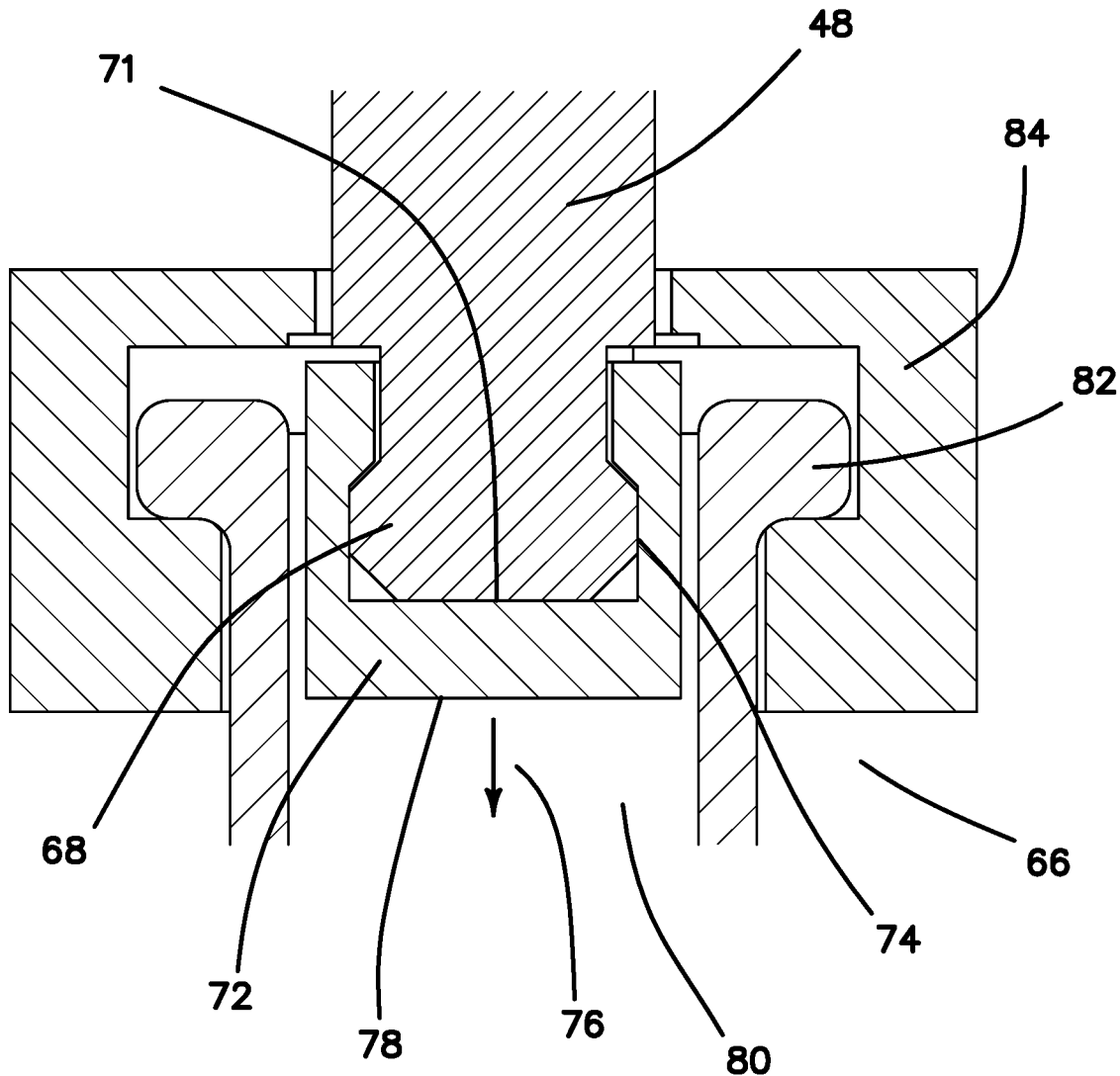
FIG. 5 is a schematic cross-sectional view of a jewel bearing that provides for low friction rotation of a plunger within a syringe.
Figure 6:
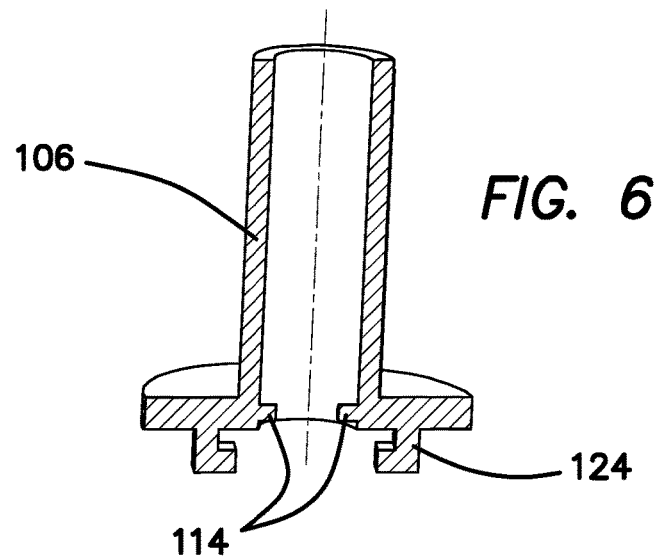
FIG. 6 illustrates a nut that rides down a fixed screw.
Figure 7:
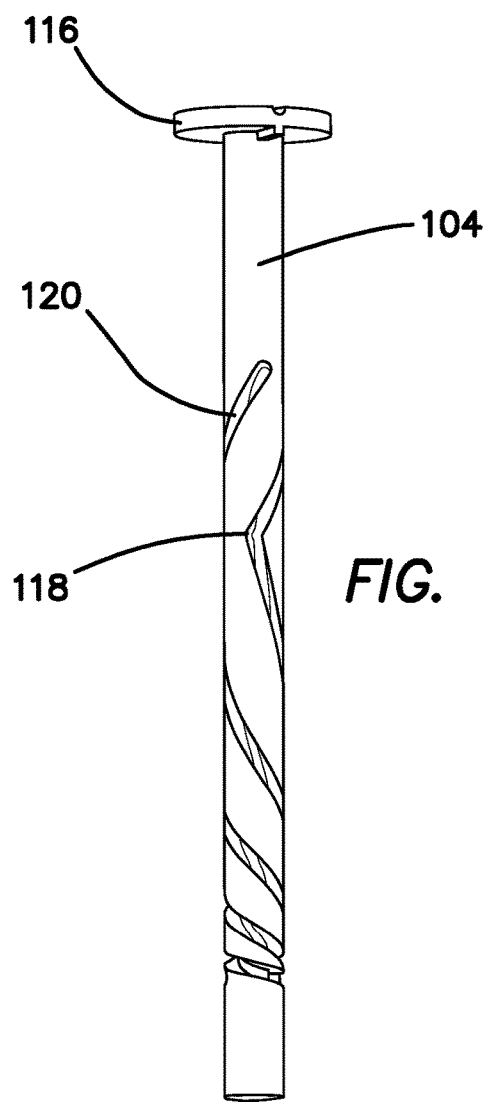
FIG. 7 illustrates a fixed screw having grooves in which pins on a nut ride down the screw.
Figure 8:
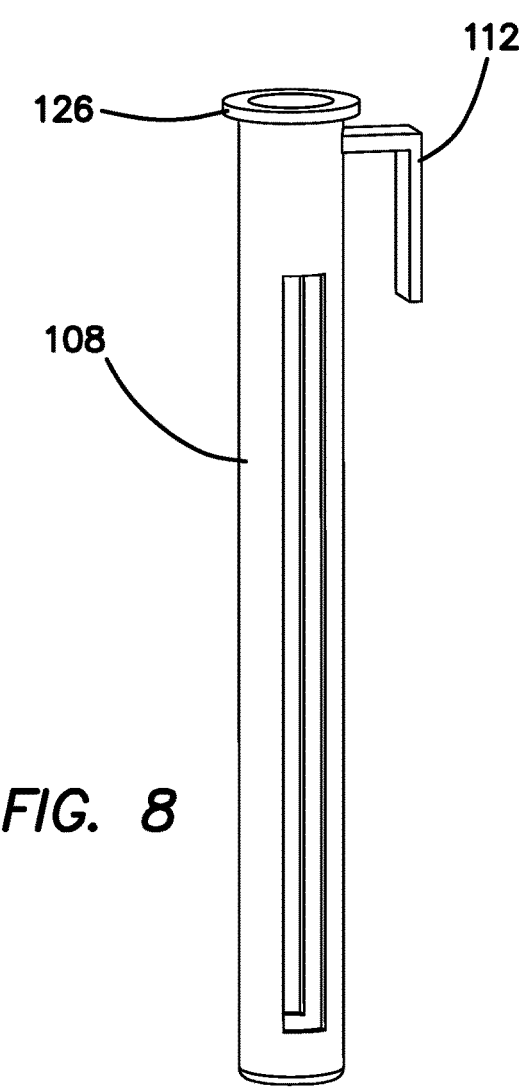
FIG. 8 illustrates a plunger.
Figure 9:
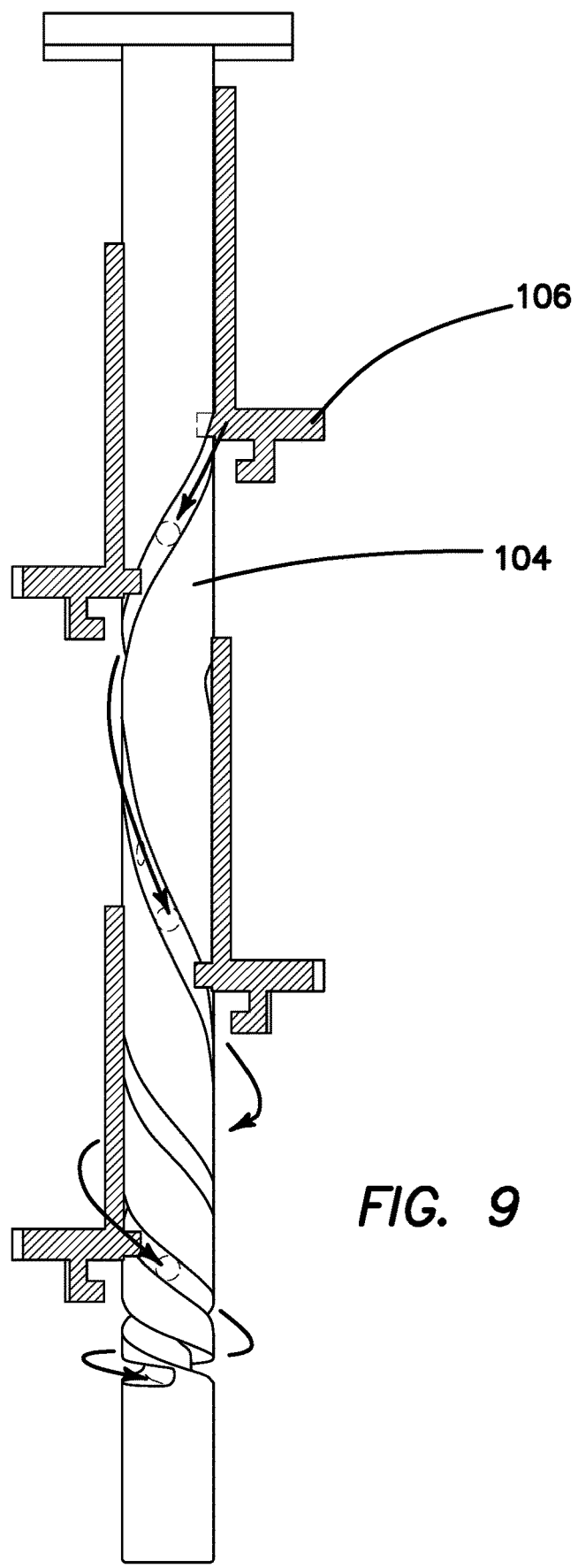
FIG. 9 illustrates motion of a nut riding down a screw.
Figure 12:
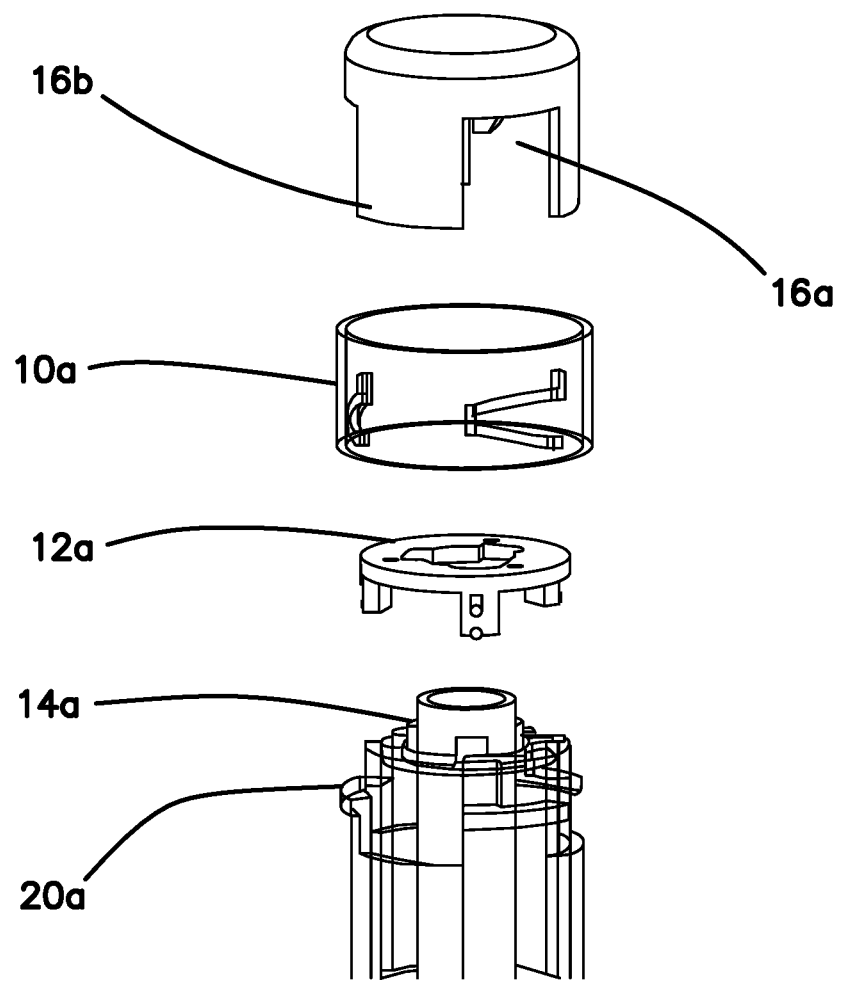
FIG. 12 illustrates an exploded view of a release button.

A schematic illustration of a bearing assembly 66 is shown in FIG. 5. The plunger rod 48 terminates at the proximal end in a knob 68. A jewel bearing 71 is formed by the knob disposed in cage 72 having a sufficiently large inner diameter to allow the presence of a small space 74 between the knob and the cage allowing the plunger rod to rotate freely while also translating down the axis of the syringe 76, and the lower surface 78 of the cage effectively forms the bottom surface of the plunger at the point in which plunger and medicament 80 in the syringe contact each other. An upper flange 82 on the syringe within clamp 84 forms a seal and maintains the connection between the syringe and the plunger rod 48 and also plunger movement assembly 62.

A drawing of a preferred embodiment of the inventive injector apparatus is illustrated in FIGS. 3 and 6-11. An elongated housing 102 contains a combination torsion and compression spring 22, a threaded screw 104, a syringe carrier 111, a nut 106 disposed around the screw, a plunger rod 108, and a syringe 110. In operation, the syringe includes a hollow needle (not shown) affixed to the proximal end of the syringe. The housing should be rigid enough to withstand a person gripping the housing without substantial deformation that would inhibit spring action. The illustrated housing only partly encloses the syringe; however, the housing could alternatively be extended to enclose the syringe and, optionally, the needle. In another alternative, the entire device could be disposed within a larger housing unit (not shown). The combination torsion and compression spring is disposed about the screw and is affixed at the distal end to the housing and at the proximal end to the nut. Prior to injection, the spring is held in place by a spring stop. For operation, the user will press a button or activate a lever, etc. (not shown) to move the spring stop and release the spring. The key 112 on the plunger rod allows the syringe to be supported prior to activation so that the needle does not protrude from the device before the user begins an injection. During storage, the key keeps it rotationally aligned with the body of the device. The nut has a generally cylindrical shape and a pair of projections 114 that ride in the threads of the screw. The spring propels the nut down the shaft of the screw. The screw is fixed within the housing, typically by a flange 116 that is affixed to the distal end of the housing. The screw has a knee 118 at that reverses the direction of the nut as it rides down the screw. In preferred embodiments, as the nut initially rides down the screw, the threads 120 are very steep so that the needle advances in a controlled manner with a relatively small force. The threads cause the nut to rotate in a direction to twist and thus store additional torsional energy in the spring. Once the needle is fully advanced, the driving force increases rapidly. In the initial phase the compression force from the spring is at its highest, then as the plunger continues to advance in the proximal direction, the compression force available from the spring drops and, after the nut passes the knee in the screw, the spring untwists and torsion energy is released causing an increase in the driving force pushing the plunger in the proximal direction.

The nut can be physically attached to the plunger rod or could press against the plunger rod (either directly or through an intervening component). In the illustrated embodiment, clip 124 secures flange 126 on the plunger 108. The motion of the nut pushes the plunger rod, which, in an initial stage pushes the syringe forward in the housing to advance the needle into the patient. The syringe could be held by a slidable disk that slides within the housing until it reaches a stop. Once the syringe is stopped, the plunger pushes medicine out of the syringe through the needle. The plunger rod is rigid, cylindrical and disposed about the screw.

In another alternative embodiment, the user can twist the spring and thus control the initial extent of torsional energy stored in the spring at the start of injection.

The selection of materials for the injector device can be selected by the skilled engineer. In some embodiments, a lubricant (such as silicone oil) is disposed between surfaces that slide over each other during operation.

The medicine within the syringe could be any solution or suspension; but the invention is especially advantageous for the delivery of a liquid having an absolute viscosity greater than 20 cP. Absolute viscosity can be measured by capillary rheometer, cone and plate rheometer, or any other known method. Preferably, the viscous solution comprises a protein suspension.

Figure 13:
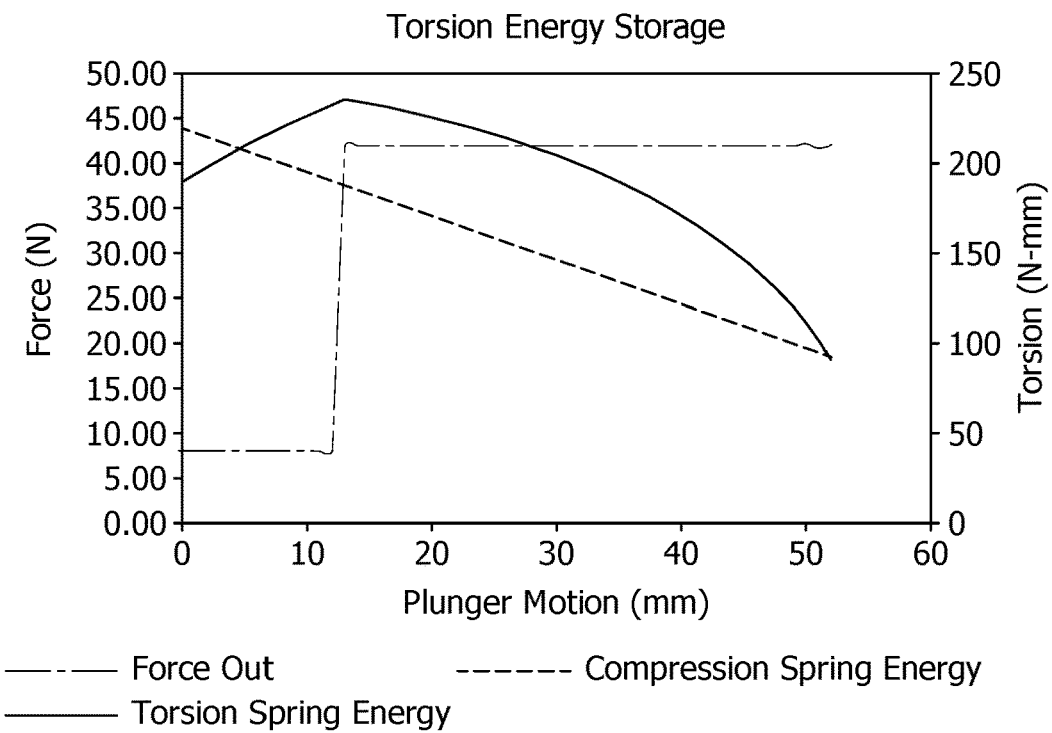
FIG. 13 is an exemplary plot of force versus plunger motion.

Exemplary plots of force versus plunger motion that are within the scope of the present invention are shown in FIG. 13. The invention includes force and/or work versus motion profiles that correlate with any of the plots described herein, either qualitatively or within 20% (or within 10%) of the values shown here. For example, the invention includes methods of injecting a medicament from a syringe possessing one or any combination of the following characteristics: an initial period of syringe motion in which the driving force is relatively low in order to insert the needle into the patient's skin (for example between about 5% to 50% of the maximum driving force and/or the average force (averaged either over the time of injection or the distance of injection) or between about 10% and about 40%, or between about 10% and 30%, or between about 15% and 30%) and in preferred embodiments this initial period is from activation of the autoinjector to 50 or 100 ms (milliseconds) after activation (or within the range of 5 ms to 50 ms), or from 0 to 5 mm, or 0 to 10 mm of plunger motion; or a speed of 200 mm/s to 4000 mm/s during the insertion; wherein during the initial phase the driving force is from 1 to Newtons (N), or from 2 to 10 N, or from 3 to 7 N; where potential torsion energy in the spring is increased over the first 50 or 100 ms after activation, or from 0 to 5 mm, or 0 to 10 mm, or from 0 to about 15 mm, or from about 0 to 25 mm; wherein potential torsion energy in the spring reaches a maximum of about 10 mm and about 7 ms (or between 5 ms and 50 ms) after activation, or between about 5 and 50 mm, or between about 5 mm and 30 mm, or between about mm to 20 mm after activation; or between about 5% to about 40% of the full distance traveled during the injection; wherein the potential torsion energy in the spring increases at least 5 N·mm or at least 10 N·mm, or between 10 and 500 N·mm, or between 15 and 300 N·mm, or between and 200 N·mm; wherein the spring is preloaded with both torsion energy and compression energy; wherein the initial potential compression energy is greater than the initial potential torsion energy; wherein the potential compression energy decreases approximately linearly as a function of plunger motion; wherein, during the second half of the injection (either by time or by plunger motion) the percentage of potential torsion energy in the spring decreases at a rate faster than the percentage of potential linear energy; wherein, after the initial phase, the driving force increases rapidly, for example, increasing at least 10 N or wherein driving force at least doubles or at least triples, over a distance of 5 mm, or 2 mm, or less, or between 0.1 to 3 mm of plunger motion, or a time of 1 s or less or between 20 ms and 1 s, or between 30 ms and 500 ms; wherein the driving force is reduced by less than 50%, more preferably less than 40%, in some embodiments less than 20% and in some embodiments between 10 and 40%, or 5 and 30% during the injection phase; wherein the driving force is remains between 10 and 200 N, or between 10 and 40 N, or between 20 and 80 N, or between 20 and 40 N during the injection phase; and wherein, from the activation step through the end of the injection phase, the potential compression energy in the spring is reduced by at least 40%, or at least 50% or from 30% to 90%.

Figure 14:
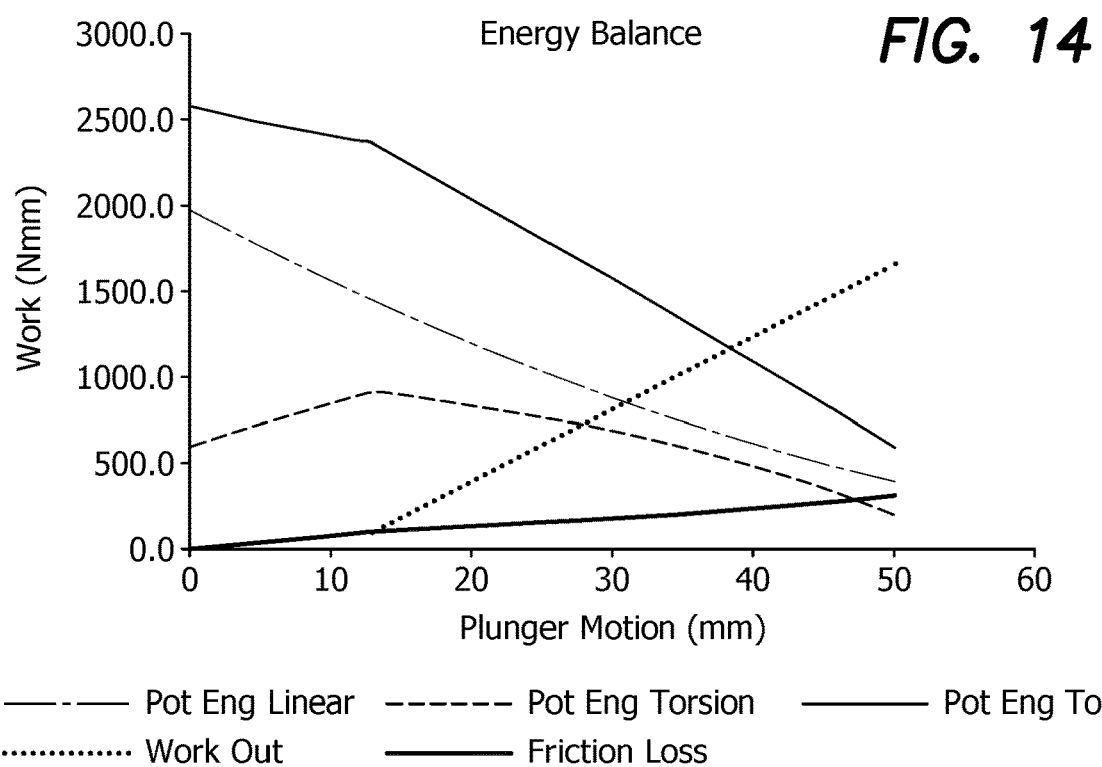
FIG. 14 is an exemplary plot of work out, potential energy of the spring (compression and torsion components) and friction loss.

An exemplary plot of work out in a preferred embodiment is shown in FIG. 14. As can be seen, after an initial stage, work out as a function of length is linear (derivation of slope is zero). Potential energy of the spring (compression and torsion components) and friction loss.

Figure 15:
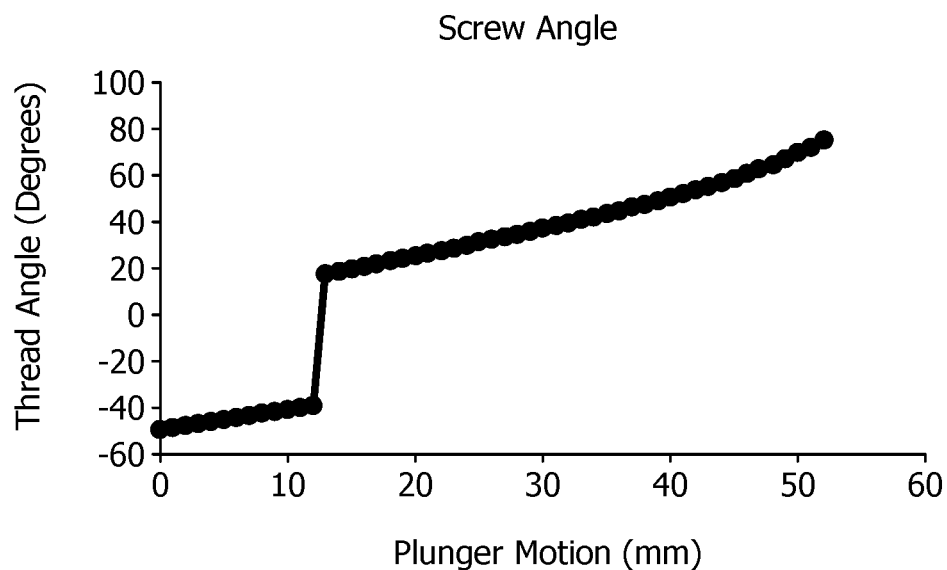
FIG. 15 is an exemplary plot of screw angle (also known as thread angle) versus plunger motion.
Figure 16:
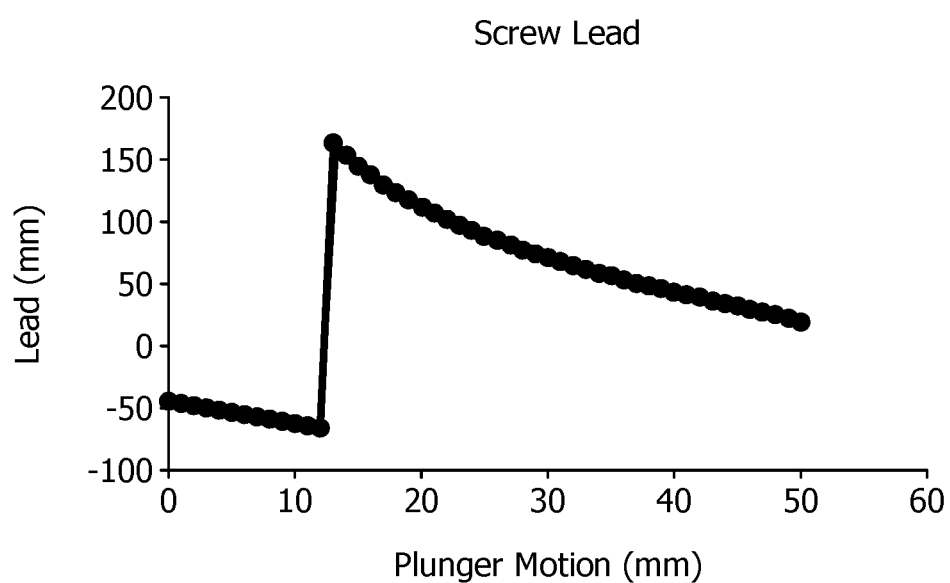
FIG. 16 is an exemplary plot of screw lead (axial travel for a single revolution) versus plunger motion.
Figure 17A:
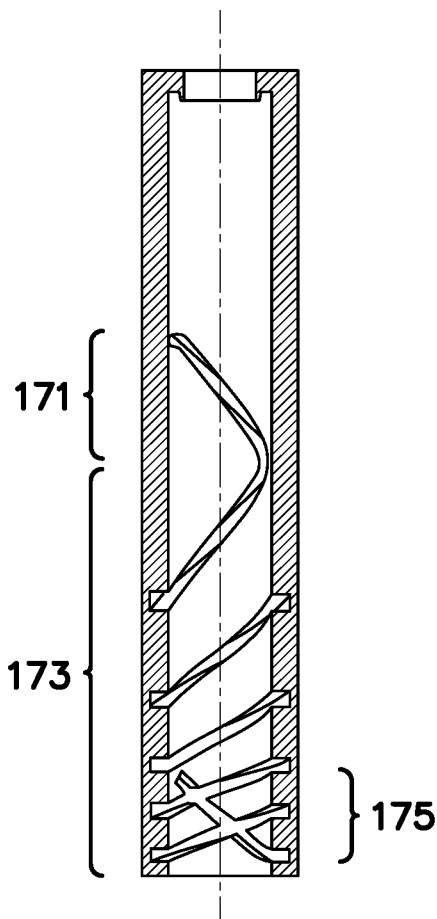
FIG. 17A shows a view of the screw with regions for needle insertion, fluid delivery, and needle retraction.
Figure 17B:
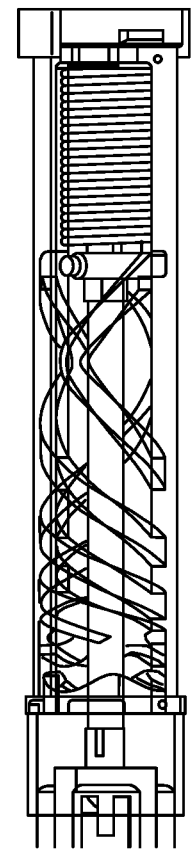
FIG. 17B is a view showing thread grooves around the central axis.

An exemplary plot of screw angle (also known as thread angle) versus plunger motion, that is within the scope of the present invention, is shown in FIG. 15. An exemplary plot of screw lead (axial travel for a single revolution) versus plunger motion, that is within the scope of the present invention, is shown in FIG. 16. These plots are not limiting but show examples of the characteristics of some preferred embodiments of the invention. In some preferred embodiments of the invention, in the initial phase, the screw angle is in the range of −70 to −20 degrees, in some embodiments from −60 to −30 degrees; then for the second (injection) phase, the screw angle is positive, in some embodiments 10 degrees or more, in some embodiments in the range between 10 and 80 degrees. In some preferred embodiments of the invention, in the initial phase, the screw's lead is negative and in some embodiments is between 10 and 120 mm, in some embodiments between 20 and 80 mm, or between 30 and 70 mm; in some embodiments, the lead decreases during the initial phase, in some preferred embodiments, this decrease is approximately monotonic, preferably with a decrease of about 5 mm to about 40 mm; then for the second (injection) phase, the screw lead is positive for at least a portion of the injection, preferably for the entire injection, and is preferably between 2 and 500 mm, in some embodiments between 10 and 300 mm, or between 15 and 200 mm; in some embodiments, the lead decreases during the second phase, in some preferred embodiments, this decrease is approximately monotonic, preferably with a decrease of at least about 20 mm or at least about mm, or in the range of about 20 mm to about 300 mm, or 10 mm to 150 mm over the length of the second phase. In some embodiments, the lead decreases during the second phase from about 170±40 mm to about 20±40 mm over the length of the second phase. The second phase refers to the injection phase.

Retraction Load Path

Figure 20:
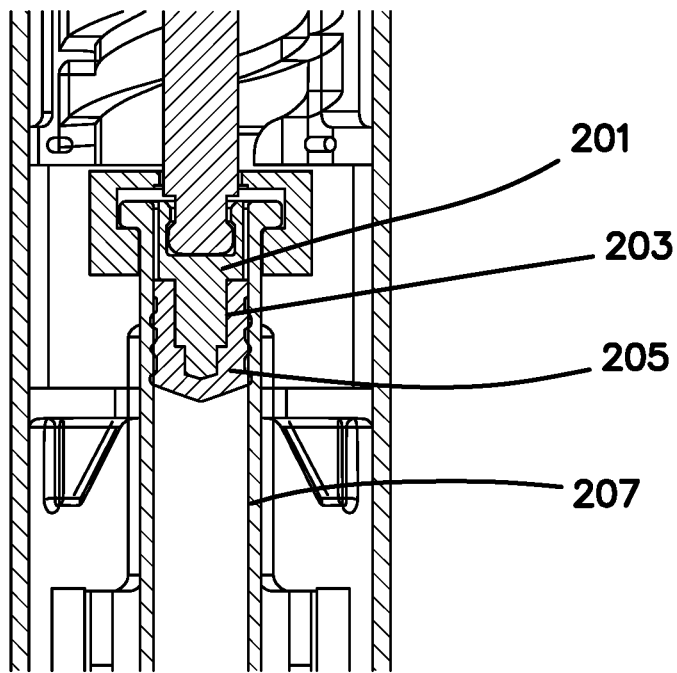
FIG. 20 shows the end of a plunger with a plunger cap.

An example of a reversing thread path and corresponding plots of force versus plunger motion, and screw angle versus plunger motion are shown in FIGS. 17-20. As described above, there is an initial portion for needle insertion 171, and a fluid delivery portion 173 where the thread path provides for relatively constant force during the course of the injection. In the illustrated embodiment, a reversing thread path 175 (needle retract) is added to provide for needle retraction at the end of the injection. During the retraction, the screw angle and force become negative; the nut reverses course and moves toward the distal end of the injector. Since there is no hydraulic load in the reverse direction, the plunger screw quickly retracts. The nut, foot, and syringe carrier all move in the distal direction on retraction. As shown in FIG. 20, the proximal end of the plunger has a foot 201, thread 203 and piston cap 205 that fits tightly within the syringe barrel 207. The friction between the plunger and the syringe barrel is typically much greater than the friction to withdraw the needle from the skin which causes the syringe to move in the reverse direction with the piston. As the syringe is withdrawn, the pressure within the syringe is quickly relieved from the syringe contents which stops delivery of fluid. At the end of the retraction, the torsion spring could lock the mechanism into a rotational detent position, thus locking the syringe in the retracted state.

Test Data

Figure 21:
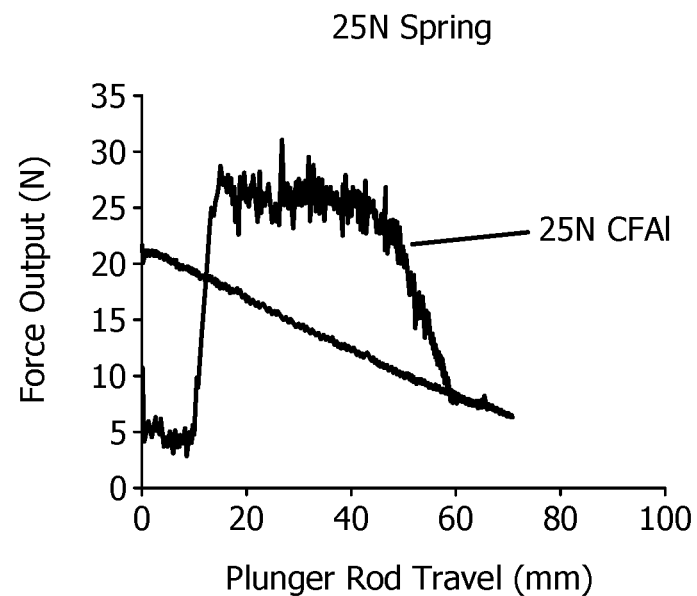
FIGS. 21-22 compare the measured force output (in N) versus distance of plunger rod travel for 25 N and 50 N combination compression/torsion springs used in the present invention and the same force springs used only in compression.
Figure 22:
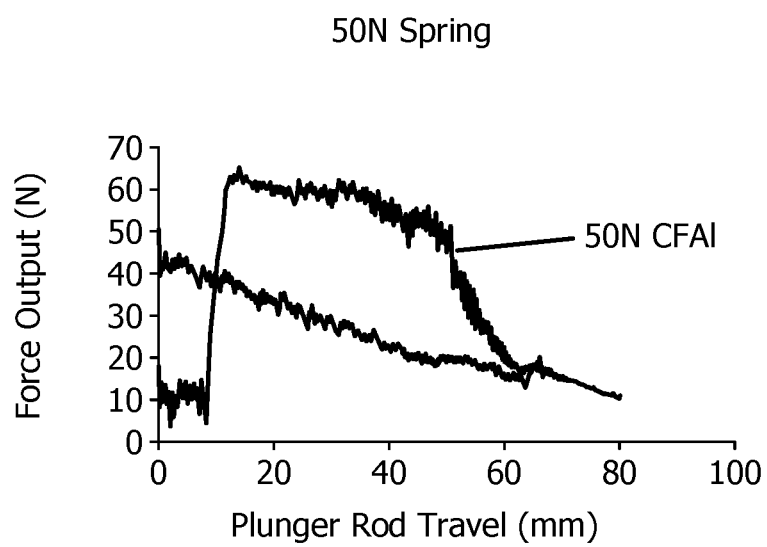

The combination compression/torsion spring was tested in conjunction with a plunger screw, nut and roller bearings. FIGS. 21-22 compare the measured force output (in N) versus distance of plunger rod travel for the combination compression/torsion springs used in the present invention and the same springs used only in compression. As can be seen, for both 25 N and 50 N springs, the combination compression/torsion springs used in the present invention provide greater and more constant force over the length of the simulated injection. The inventive configuration provided a near plateau, with less than a 20% decrease in force over the length of a simulated injection while the straight compression spring shows about a 50% decrease in force over the length of the simulated injection. As a result, the inventive configuration will provide a faster, smoother, and/or more complete injection as compared with a device powered by a conventional compression spring.

Figure 24:
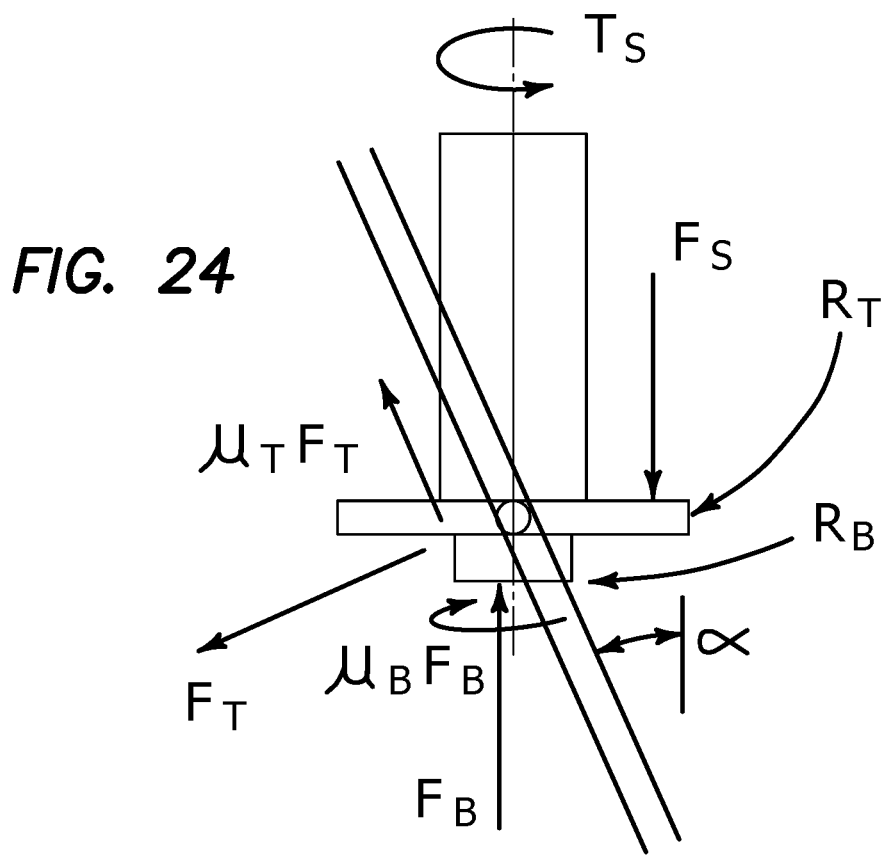
FIGS. 23-25 show geometry and forces of a free body analysis of a preferred embodiment of the invention.
Figure 23:
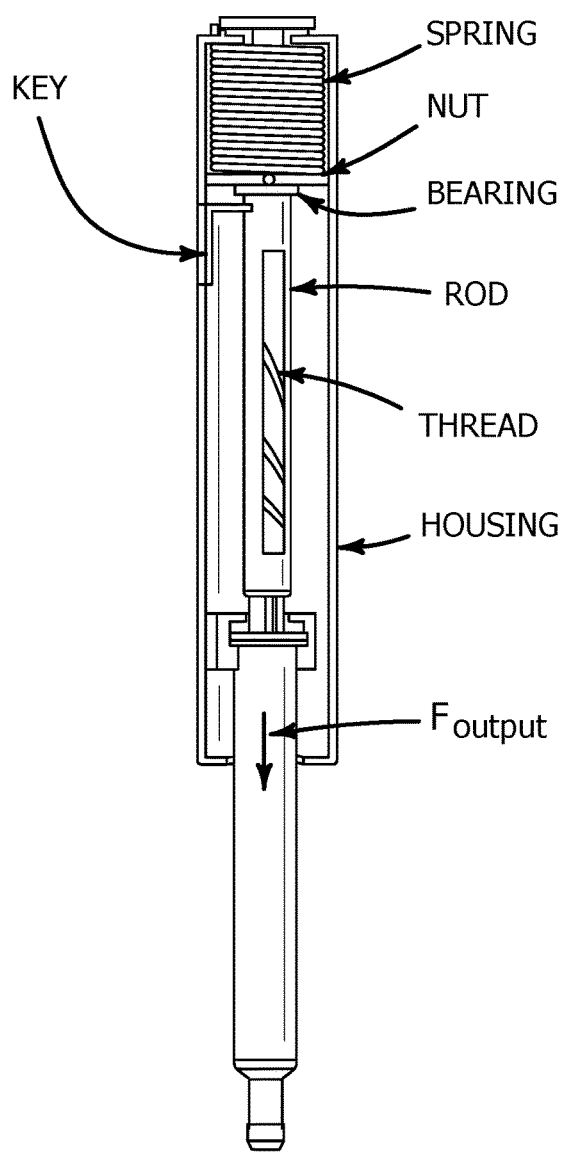
Figure 25:
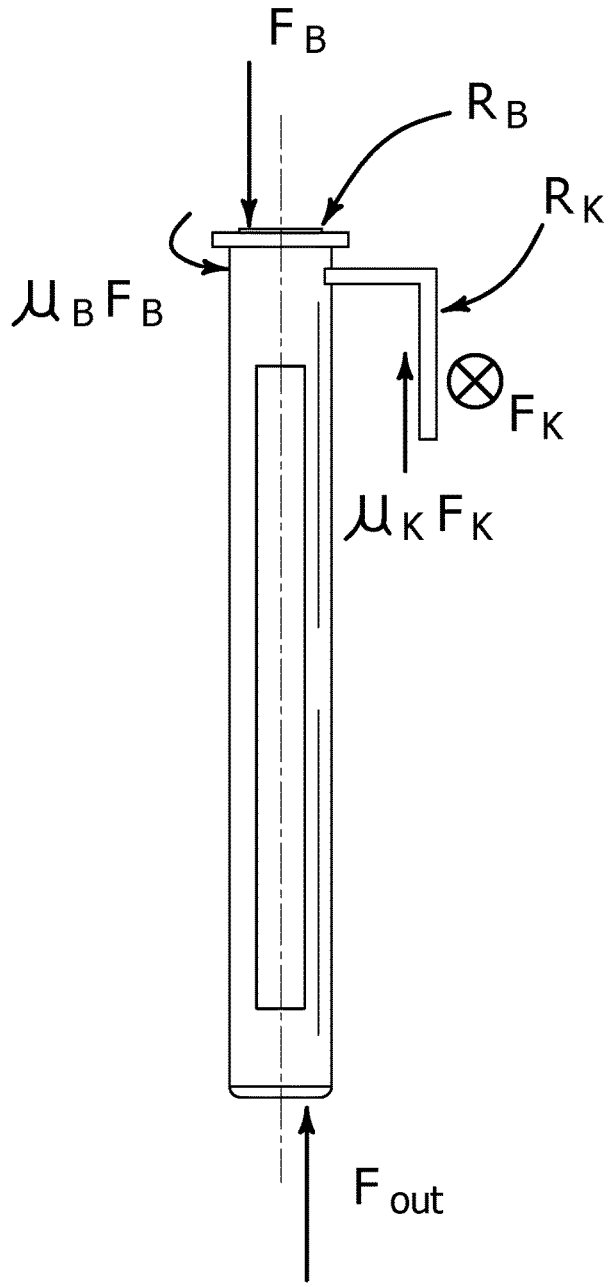

A free body diagram analysis is useful for determining forces, torques and friction loads on the autoinjector mechanism based on the characteristics of the geometry (i.e. radius, thread pitch, etc.) By taking each component and examining the applied forces and torques at each physical interface, a mathematical relationship can be developed. From these equations, the characteristics can be explored and the design can be adjusted to achieve the desired results. The free body analysis presented below was used to develop the theoretical performance curves presented in FIGS. 13 through 16 based on a preferred embodiment. FIGS. 23 through 25 show the preferred ranges of forces, torques, energy and screw geometry.

In some instances, preferred embodiments of the invention can be characterized by the following geometry including a threaded screw and the corresponding equations: The following list of terms relates to the embodiment having the type of geometry illustrated in FIGS. A-C.

$F_s$=force applied by spring
$T_s$=torque applied by spring
$F_T$=force on thread
$R_T$=radius of thread
$\mu_T$=friction coefficient of thread
$\alpha$=angle of thread
$F_B$=force on bearing
$R_B$=radius of bearing
$\mu_B$=friction coefficient of bearing
$F_K$=force on key
$R_K$=radius of key
$\mu_k$=friction coefficient of key
$F_{out}$=force output The various forces and torques in the autoinjector can be understood using free body diagrams as follows:

Free body diagram of the Nut:
Sum of forces in the Y direction must equal zero:

$$(\mu_T F_T)\cos\alpha - F_T\sin\alpha + F_B - F_s = 0$$

$$F_T = (F_s - F_B)/((\mu_T)\cos\alpha - \sin\alpha)$$

Sum of torques must equal zero:

$$T_s - (\mu_T F_T R_T)\sin\alpha - (F_T R_T)\cos\alpha - \mu_B F_B R_B = 0$$

$$T_s = F_T R_T((\mu_T)\sin\alpha + \cos\alpha) + \mu_B F_B R_B$$

Combining forces and torques:

$$T_s = R_T(F_s - F_B)/(((\mu_T)\sin\alpha + \cos\alpha)/((\mu_T)\cos\alpha - \sin\alpha)) + \mu_B F_B R_B$$

$$\beta = ((\mu_T)\sin\alpha + \cos\alpha)/((\mu_T)\cos\alpha - \sin\alpha) = ((\mu_T)\operatorname{Tan}\alpha + 1)/(\mu_T - \operatorname{Tan}\alpha)$$

$$F_B = (T_s - R_T F_s \beta)/\mu_B R_B - R_T \beta)$$

Free Body Diagram of the plunger rod:
Sum of torques must equal zero:

$$\mu_B F_B R_B = F_K R_K$$

$$F_K = \mu_B F_B R_B / R_K$$

Sum of forces must equal zero:

$$F_{out}=F_B-\mu_K F_K$$

Combining forces and torques:

$$F_{out}=F_B(1-\mu_K\mu_B R_B/R_K)$$

In some embodiments, the inventive methods and apparatus may be characterized by full or partial conformance with the features described in the forgoing free body analysis.

What is claimed is:

1. A method of injecting a medicament from a syringe, comprising:
   providing a driving force that moves a plunger down the syringe from a distal position toward a proximal position;
   wherein a torsion spring is attached at a distal end to a first surface and at a proximal end to a second surface;
   wherein the second surface moves with the plunger;
   wherein an early stage movement of the plunger toward the proximal position twists the torsion spring to store energy in the torsion spring;
   and, subsequently, at a later stage, as the driving force continues to move the plunger toward the proximal position, and the second surface moves with the plunger, the torsion spring rotates through a prescribed path to modify the driving force moving the plunger toward the proximal position.

2. The method of claim 1 wherein the torsion spring is a combination torsion and compression spring.

3. The method of claim 2 wherein the combination torsion and compression spring is the only source of providing the driving force.

4. The method of claim 3 further comprising a retraction stage, subsequent to the later stage, in which the combination torsion and compression spring pulls the plunger in the distal direction.

5. The method of claim 4 wherein the second surface is on a nut, wherein the combination torsion and compression spring is attached to the nut and wherein the prescribed path is controlled by a screw having helical threads;
   wherein the nut has a pin or pins that ride in the helical threads of the screw;
   wherein, during the retraction stage, the pin or pins ride in the helical threads in a distal direction and wherein the combination torsion and compression spring provides a torque having a force component in the direction in which the pin or pins ride.

6. The method of claim 2 wherein, during the later stage, the combination torsion and compression spring is untwisted to enhance the driving force.

7. The method of claim 2 wherein, once activated, the injection occurs without any power source other than the combination torsion and compression spring.

8. The method of claim 2 wherein the early stage movement corresponds to an initial period of syringe motion in which the driving force is relatively low in order to insert a needle into a patient's skin and wherein:
   this initial period is from activation of the syringe to 50 or 100 ms after activation; or
   the initial period is from 0 to 5 mm, or 0 to 10 mm of plunger motion; or
   during the initial period, the driving force is from 1 to 20 N, or from 2 to 10 N, or from 3 to 7 N.

9. The method of claim 2 wherein potential torsion energy in the combination torsion and compression spring is increased over the first 50 ms after activation; or
   wherein potential torsion energy in the combination torsion and compression spring reaches a maximum:
   between about 10 ms and about 1 s after activation; or
   between about 5 and 50 mm after activation; or
   between about 5% to about 40% of the full distance traveled during the injection;
   or wherein the potential torsion energy in the combination torsion and compression spring increases at least 5 N·mm.

10. The method of claim 2 wherein the combination torsion and compression spring is preloaded with both torsion energy and compression energy.

11. The method of claim 10 wherein the initial potential compression energy is greater than the initial potential torsion energy.

12. The method of claim 2 wherein potential compression energy in the combination torsion and compression spring decreases approximately linearly as a function of plunger motion; or
   wherein, during a second half of the injection (either by time or by plunger motion) a percentage of potential torsion energy in the combination torsion and compression spring decreases at a rate faster than a percentage of potential linear energy; or
   wherein, after an initial phase, the driving force increases rapidly by at least 10 N; or
   wherein, after the initial phase, the driving force at least doubles or at least triples:
   over a distance of 5 mm, or 2 mm, or less: or
   between 0.1 to 3 mm of plunger motions: or
   a time of 1 s or less or between 20 ms and 1 s; or
   between 30 ms and 500 ms;
   or any combination of these.

13. The method of claim 2 wherein a later stage movement defines an injection phase, and
   wherein the driving force is reduced by less than 50% or between 5 and 30% during the injection phase; or
   wherein the driving force i-s-remains between 10 and 200 N, or between 10 and 40 N, or between 20 and 80 N, or between 20 and 40 N during the injection phase.

14. The method of claim 2 wherein, from an activation step through an end of an injection phase, potential compression energy in the combination torsion and compression spring is reduced by at least 40%, or at least 50% or from 30% to 90%.

15. The method of claim 1 wherein the torsion spring is attached to a nut and wherein the prescribed path is controlled by a screw having helical threads;
   wherein the nut has a pin or pins that ride in the helical threads of the screw;
   wherein the helical threads have a thread angle α that varies along the length of the screw.

16. A method of injecting a medicament from a syringe, comprising:
   providing a driving force that inserts a needle into skin of a patient at a proximal end of the syringe, then subsequently moves a plunger down the syringe from a distal position toward a proximal position;
   wherein a spring having both a torsion mode and a compression mode is attached at one first end to a first surface and at one second end to a second surface;
   wherein the second surface moves with the plunger and an early stage movement of the plunger toward the proximal position twists the spring to store energy in the spring;
   and subsequently as the driving force due to the compression mode continues to move the plunger toward the proximal position, and the second surface moves with the plunger, the torsion mode of the spring rotates through a prescribed path to modify the driving force moving the plunger toward the proximal position.

17. The method of claim 16 wherein the insertion of the needle is accomplished by transferring energy from the compression mode of the spring to the torsion mode of the spring in order to optimize force needed for needle insertion.

18. The method of claim 16 wherein the spring comprises a coil wire with a square cross section.

19. The method of claim 16 wherein the step in which the torsion mode of the spring rotates through the prescribed path to modify the driving force comprises untwisting the spring to release energy from the spring to enhance the driving force moving the plunger toward the proximal position.

* * * * *